(12) United States Patent
Jacob

(10) Patent No.: US 11,744,531 B2
(45) Date of Patent: Sep. 5, 2023

(54) SYSTEMS AND METHODS FOR FOCAL SPOT MOTION DETECTION IN BOTH X- AND Y-DIRECTIONS AND CORRECTION

(71) Applicant: GE PRECISION HEALTHCARE LLC, Wauwatosa, WI (US)

(72) Inventor: Biju Jacob, Niskayuna, NY (US)

(73) Assignee: GE Precision Healthcare LLC, Wauwatosa, WI (US)

(*) Notice: Subject to any disclaimer, the term of this patent is extended or adjusted under 35 U.S.C. 154(b) by 157 days.

(21) Appl. No.: 17/361,699

(22) Filed: Jun. 29, 2021

(65) Prior Publication Data

US 2022/0409152 A1 Dec. 29, 2022

(51) Int. Cl.
*A61B 6/00* (2006.01)
*A61B 6/03* (2006.01)

(52) U.S. Cl.
CPC .......... *A61B 6/4021* (2013.01); *A61B 6/032* (2013.01); *A61B 6/5205* (2013.01)

(58) Field of Classification Search
CPC ..... A61B 6/4291; A61B 6/032; A61B 6/4233; A61B 6/4021; A61B 6/58; A61B 6/5205; A61B 6/585; A61B 6/587; A61B 6/06; A61B 6/4476; A61B 6/583; A61B 6/145; A61B 6/14; A61B 6/4411; A61B 6/5217; A61B 6/425; A61B 6/4007; A61B 6/4035; A61B 6/547; A61B 6/461; A61B 6/582; A61B 6/4405; A61B 6/025; A61B 6/5258; A61B 6/584; A61B 6/588; A61B 6/545; A61B 6/08; A61B 6/5252; A61B 6/4071; G01T 1/1648; G01T 1/29; G01T 1/2928; G01T 1/16; G01T 7/005; G01T 1/2985; H01J 37/244; G01N 23/046; G01N 2223/303; G01N 2223/33; G01N 23/04; G01N 2223/3035; G06T 11/005; G06T 2211/40; G06T 2211/421; G06T 5/20; G06T 211/432; G21K 1/025; G21K 1/02; G01B 15/00

USPC ............................................ 378/4, 147–153
See application file for complete search history.

(56) References Cited

U.S. PATENT DOCUMENTS

| | | | | |
|---|---|---|---|---|
| 5,657,364 | A * | 8/1997 | Pfoh .................... | A61B 6/4021 378/4 |
| 2004/0120464 | A1 * | 6/2004 | Hoffman ................ | G21K 1/025 378/147 |
| 2011/0176663 | A1 * | 7/2011 | Shaughnessy ......... | A61B 6/032 378/207 |
| 2011/0188624 | A1 * | 8/2011 | Ren .......................... | G21K 1/02 378/150 |

(Continued)

*Primary Examiner* — Irakli Kiknadze
(74) *Attorney, Agent, or Firm* — Fletcher Yoder, P.C.

(57) ABSTRACT

A method for estimating motion of an X-ray focal spot is provided. The acts of the method include acquiring image data by causing X-rays to be emitted from the X-ray focal spot of an X-ray source toward a radiation detector comprising multiple channels, wherein a subset of the channels each have a collimator blade positioned above the respective channel. The acts of the method also include independently estimating X-ray focal spot motion in an X-direction for the X-ray focal spot relative to an isocenter of the radiation detector and in a Y-direction along a direction of the X-rays for the X-ray focal spot relative to the isocenter based on respective channel gains for a first channel and a second channel of the subset of the channels.

20 Claims, 9 Drawing Sheets

(56) References Cited

U.S. PATENT DOCUMENTS

2012/0328076 A1* 12/2012 Ikhlef ................... G21K 1/025
                                                                  378/62
2017/0278277 A1*  9/2017 Morf ...................... A61B 6/032
2020/0088891 A1*  3/2020 Abraham ............. G01N 23/046
2021/0177372 A1   6/2021 Jacob et al.

* cited by examiner

SYSTEMS AND METHODS FOR FOCAL SPOT MOTION DETECTION IN BOTH X- AND Y-DIRECTIONS AND CORRECTION

BACKGROUND

Embodiments of the present specification relate generally to X-ray based imaging techniques, and more particularly to issues related to mis-alignment of an X-ray emission point and X-ray detector elements.

In an X-ray based imaging system, such as a computed tomography (CT) imaging system, an X-ray beam is emitted towards an object such as a patient or item (e.g., package, manufactured item, and so forth) to image a region of interest in the object. The beam is typically attenuated as it passes through the object. Subsequently, the attenuated beam is incident on a radiation detector having an array of detector elements. In response to the attenuated beam, the detector elements of the array generate respective electrical signals representative of internal information of the object. These electrical signals are processed by a data processing unit to generate an image representative of the region of interest in the object.

Reconstruction of images from the acquired data is generally based upon the assumption that X-ray photons have traveled in a straight path from an X-ray emission focal spot to the detector element at which the respective photon is detected. However, mis-alignment or movement of the X-ray focal spot with respect to one or more collimating elements or plates (e.g., a post-patient anti-scatter grid) may result in image artifacts that are detrimental to clinical use of imaging systems, such as CT imaging systems. This effect may be more significant in systems where the collimator blade pitch is larger than the channel (i.e., pixel) pitch, such that different channels may be effected to different degrees by the "shadow" case by the respective collimator blades.

BRIEF DESCRIPTION

Certain embodiments commensurate in scope with the originally claimed subject matter are summarized below. These embodiments are not intended to limit the scope of the claimed subject matter, but rather these embodiments are intended only to provide a brief summary of possible embodiments. Indeed, the invention may encompass a variety of forms that may be similar to or different from the embodiments set forth below.

In one embodiment, a method for estimating motion of an X-ray focal spot is provided. The acts of the method include acquiring image data by causing X-rays to be emitted from the X-ray focal spot of an X-ray source toward a radiation detector comprising multiple channels, wherein a subset of the channels each have a collimator blade positioned above the respective channel. The acts of the method also include independently estimating X-ray focal spot motion in an X-direction for the X-ray focal spot relative to an isocenter of the radiation detector and in a Y-direction along a direction of the X-rays for the X-ray focal spot relative to the isocenter based on respective channel gains for a first channel and a second channel of the subset of the channels.

In another embodiment, an imaging system is provided. The imaging system includes an X-ray source configured to emit X-rays from an X-ray focal spot during operation, a collimator including multiple collimator blades, and a radiation detector, including multiple pixels, each pixel corresponding to a channel of the radiation detector, wherein a subset of the channels each have a collimator blade positioned above the respective channel. The imaging system also includes processing circuitry configured to perform acts. The acts include acquiring image data by causing X-rays to be emitted from the X-ray source toward the radiation detector. The acts also include independently estimating X-ray focal spot motion in an X-direction for the X-ray focal spot relative to an isocenter of the radiation detector and in a Y-direction for the X-ray focal spot relative to the isocenter based on respective channel gains for a first channel and a second channel of the subset of the channels.

In a further embodiment, a non-transitory computer-readable medium, the computer-readable medium including processor-executable code that when executed by a processor, causes the processor to perform acts. The acts include acquiring image data by causing X-rays to be emitted from an X-ray focal spot of an X-ray source toward a radiation detector including multiple channels, wherein a subset of the channels each have a collimator blade positioned above the respective channel. The acts also include simultaneously measuring a respective channel gain for a first channel and a second channel of the subset of channels disposed on opposite sides of an isocenter of the radiation detector. The acts further include independently estimating X-ray focal spot motion in an X-direction for the X-ray focal spot relative to the isocenter and in a Y-direction for the X-ray focal spot relative to the isocenter based on the respective channel gains for the first channel and the second channel.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While aspects of the following discussion may be provided in the context of medical imaging, it should be appreciated that the present techniques are not limited to such medical contexts. Indeed, the provision of examples and explanations in such a medical context is only to facilitate explanation by providing instances of real-world implementations and applications. However, the present approaches may also be utilized in other contexts, such as tomographic image reconstruction for industrial Computed Tomography (CT) used in non-destructive inspection of manufactured parts or goods (i.e., quality control or quality review applications), and/or the non-invasive inspection of packages, boxes, luggage, and so forth (i.e., security or screening applications). In general, the present approaches may be useful in any imaging or screening context or image processing field mis-alignment of an X-ray emission point may be mis-aligned with an array of detector elements having associated anti-scatter or collimation elements (e.g., blades).

As discussed herein, reconstruction of images from the acquired X-ray transmission data is generally based upon the assumption that X-ray photons have traveled in a straight path from an X-ray emission focal spot to the detector element at which the respective photon is detected. However, mis-alignment or movement of the X-ray focal spot with respect to one or more collimating elements or plates (e.g., a post-patient anti-scatter grid) may result in image artifacts that are detrimental to clinical use of imaging systems, such as CT imaging systems. This effect may be more pronounced in systems where the collimator blade pitch is larger than the channel (i.e., pixel) pitch.

The techniques disclosed may be used to detect and correct channel gain errors resulting from X-ray focal spot mis-alignment during the course of a scan, which may result in the noted image artifacts. One benefit of the techniques described herein relative to conventional techniques is that they do not require additional hardware for detection of focal spot drift. Instead, the methods described herein take into account the static mis-alignment of each blade during manufacturing as part of estimating and correcting X-ray focal spot drift or mis-alignment. In this manner, the risk of image artifacts due to focal spot motion is reduced and the need for costly hardware solutions to detect focal spot motion is avoided.

Figure 1:
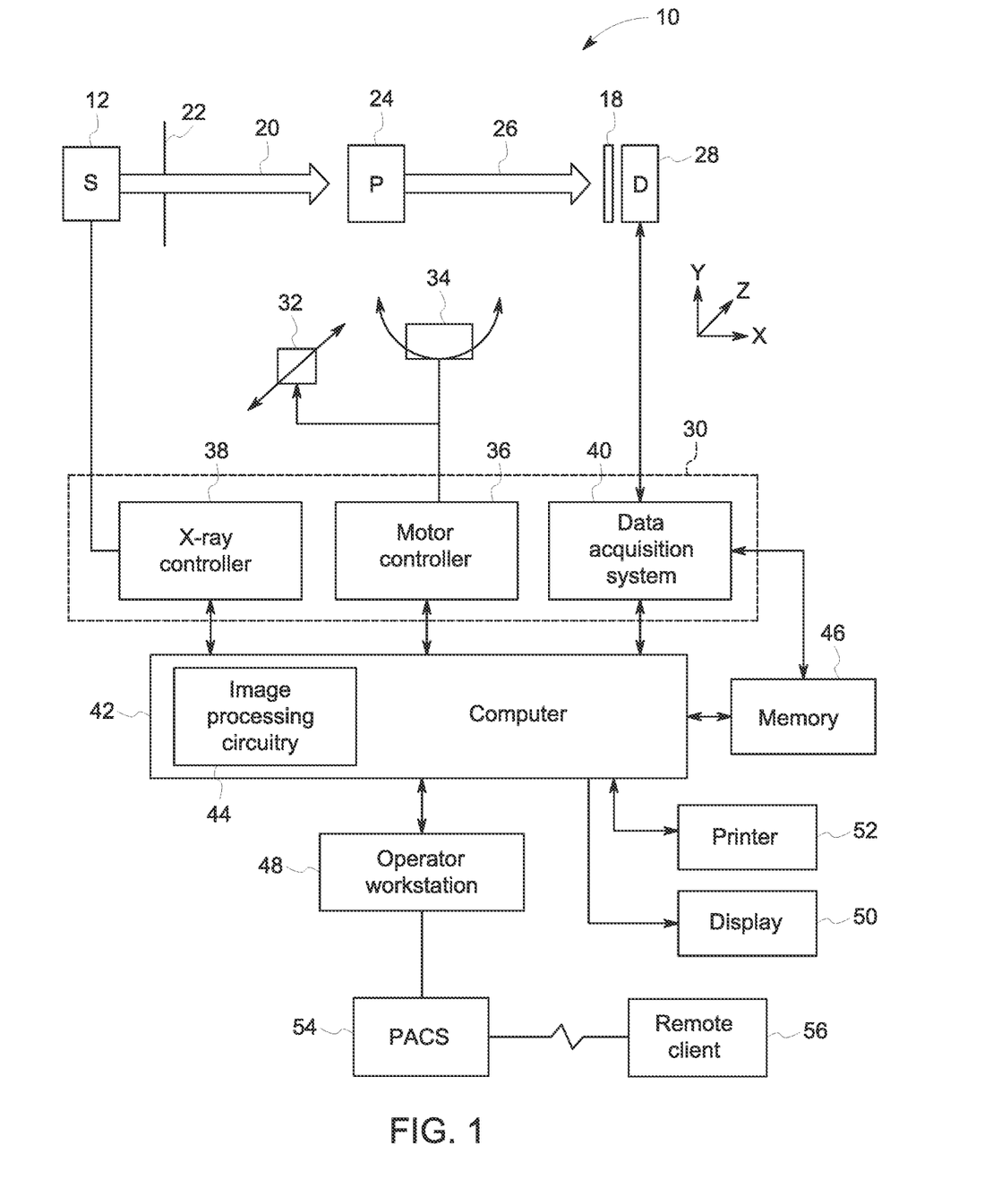
FIG. 1 depicts components of a computed tomography imaging system, in accordance with certain aspects of the present disclosure.

With the preceding discussion in mind, FIG. 1 illustrates an embodiment of an imaging system 10 for acquiring and processing image data in accordance with structures and approaches discussed herein. In the illustrated embodiment, system 10 is a computed tomography (CT) system designed to acquire X-ray projection data and to reconstruct the projection data into volumetric reconstructions for display and analysis. The CT imaging system 10 includes one or more X-ray sources 12, such as one or more X-ray tubes or solid state emission structures which allow X-ray generation at one or more energy spectra during an imaging session.

In certain implementations, the source 12 may be positioned proximate to a pre-patient collimator and/or filter assembly 22 that may be used to steer the X-ray beam 20, to define the shape (such as by limiting off-angle emissions) and/or extent of a high-intensity region of the X-ray beam 20, to control or define the energy profile of the X-ray beam 20, and/or to otherwise limit X-ray exposure on those portions of the patient 24 not within a region of interest. In practice, the filter assembly or beam shaper 22 may be incorporated within the gantry, between the source 12 and the imaged volume.

The X-ray beam 20 passes into a region in which the subject (e.g., a patient 24) or object of interest (e.g., manufactured component, baggage, package, and so forth) is positioned. The subject attenuates at least a portion of the X-ray photons 20, resulting in attenuated X-ray photons 26 that impinge upon a pixelated detector array 28 formed by a plurality of detector elements (e.g., pixels) arranged in an m×n array. In the depicted example, the attenuated X-ray photons 26 pass through a collimator 18 (e.g., an anti-scatter grid) prior to reaching the detector array 28. As discussed herein, the collimator 18 may consist of a plurality of blades or other elements aligned substantially perpendicular to the surface of the detector array 28 and formed from an attenuating material that limit or prevent X-ray photons 26 traveling at off-angles (e.g., scattered X-rays) from reaching the detector array 28. The electrical signals reaching the detector array 28 are detected and processed to generate one or more projection datasets. In the depicted example, the detector 28 is coupled to the system controller 30, which commands acquisition of the digital signals generated by the detector 28.

A system controller 30 commands operation of the imaging system 10 to execute filtration, examination and/or calibration protocols, and may process the acquired data. With respect to the X-ray source 12, the system controller 30 furnishes power, focal spot location, control signals and so forth, for the X-ray examination sequences. In accordance with certain embodiments, the system controller 30 may control operation of the filter assembly 22, the CT gantry (or other structural support to which the X-ray source 12 and detector 28 are attached), and/or the translation and/or inclination of the patient support over the course of an examination.

In addition, the system controller 30, via a motor controller 36, may control operation of a linear positioning subsystem 32 and/or a rotational subsystem 34 used to move the subject 24 and/or components of the imaging system 10, respectively. For example, in a CT system, the radiation source 12 and detector 28 rotate about the object (e.g., patient 24) to acquire X-ray transmission data over a range of angular views. Thus, in a real-world implementation, the imaging system 10 is configured to generate X-ray transmission data corresponding to each of the plurality of angular positions (e.g., 360°, 180°+ a fan beam angle (α), and so forth) covering an entire scanning area of interest.

The system controller 30 may include signal processing circuitry and associated memory circuitry. In such embodiments, the memory circuitry may store programs, routines, and/or encoded algorithms executed by the system controller 30 to operate the imaging system 10, including the X-ray source 12 and/or filter assembly 22, and to process the digital measurements acquired by the detector 28 in accordance with the steps and processes discussed herein. In one embodiment, an algorithm be stored in the memory circuitry and executed by a processor to X-ray focal spot motion in both an X-direction relative to an isocenter of the detector 28 and in a Y-direction relative to the isocenter of the detector 28. In one embodiment, the system controller 30 may be implemented as all or part of a processor-based system.

The source 12 may be controlled by an X-ray controller 38 contained within the system controller 30. The X-ray controller 38 may be configured to provide power, timing signals, and/or focal spot size and spot locations to the source 12. In addition, in some embodiments the X-ray controller 38 may be configured to selectively activate the source 12 such that tubes or emitters at different locations within the system 10 may be operated in synchrony with one another or independent of one another or to switch the source between different energy profiles during an imaging session.

The system controller 30 may include a data acquisition system (DAS) 40. The DAS 40 receives data collected by readout electronics of the detector 28, such as digital signals from the detector 28. The DAS 40 may then convert and/or process the data for subsequent processing by a processor-based system, such as a computer 42. In certain implementations discussed herein, circuitry within the detector 28 may convert analog signals of the detector to digital signals prior to transmission to the data acquisition system 40. The computer 42 may include or communicate with one or more non-transitory memory devices 46 that can store data processed by the computer 42, data to be processed by the computer 42, or instructions to be executed by image processing circuitry 44 of the computer 42. For example, a processor of the computer 42 may execute one or more sets of instructions stored on the memory 46, which may be a memory of the computer 42, a memory of the processor, firmware, or a similar instantiation. By way of example, the image processing circuitry 44 of the computer 42 may be configured to generate a diagnostic image. In one embodiment, the diagnostic image is a real-time image obtained using image reconstruction techniques applied to the plurality of signals obtained from the plurality of pixels 102 and corrected for X-ray focal spot motion or mis-alignment. In one embodiment, the diagnostic image is a CT image corrected for X-ray focal spot motion or mis-alignment and displayed on a display device 50 for assisting a medical practitioner.

The computer 42 may also be adapted to control features enabled by the system controller 30 (i.e., scanning operations and data acquisition), such as in response to commands and scanning parameters provided by an operator via an operator workstation 48. The system 10 may also include a display 50 coupled to the operator workstation 48 that allows the operator to view relevant system data, imaging parameters, raw imaging data, reconstructed data or images, and so forth. Additionally, the system 10 may include a printer 52 coupled to the operator workstation 48 and configured to print any desired measurement results. The display 50 and the printer 52 may also be connected to the computer 42 directly (as shown in FIG. 1) or via the operator workstation 48. Further, the operator workstation 48 may include or be coupled to a picture archiving and communications system (PACS) 54. PACS 54 may be coupled to a remote system or client 56, radiology department information system (RIS), hospital information system (HIS) or to an internal or external network, so that others at different locations can gain access to the image data.

Figure 2:
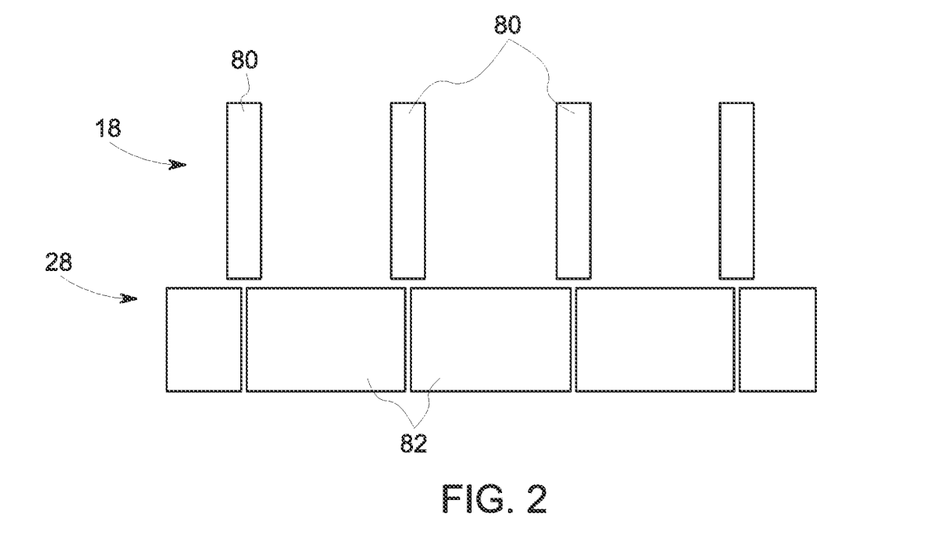
FIG. 2 depicts schematically a side-view of channels of a detector on which collimator blades are disposed, in accordance with certain aspects of the present disclosure.

With the preceding discussion of an overall imaging system 10 in mind, and turning to FIG. 2, an example of a prior detector 28 and collimator 18 arrangement is shown in a cut-away side view. In this example, the detector 28 is shown as including an array of pixels 82 each corresponding to a readout channel. In one such example, the pixel pitch may be approximately 1 mm. A set of collimator blades 80 are shown associated with the array of pixels 82 such that each pixel is separately collimated. The blades 80 are shown as being placed at where pixels are joined, such that shadowing attributable to the blades 80 is primarily at these joins, leaving the majority of the active area of the pixels 82 relatively free of shadows produced by the blades. In this manner, each pixel 82 is effected relatively consistently and uniformly by the collimator blades 80. In particular, if an X-ray emission focal spot is mis-aligned, the differential gain change attributable to the mis-alignment between adjacent channels is relatively small.

Figure 3:
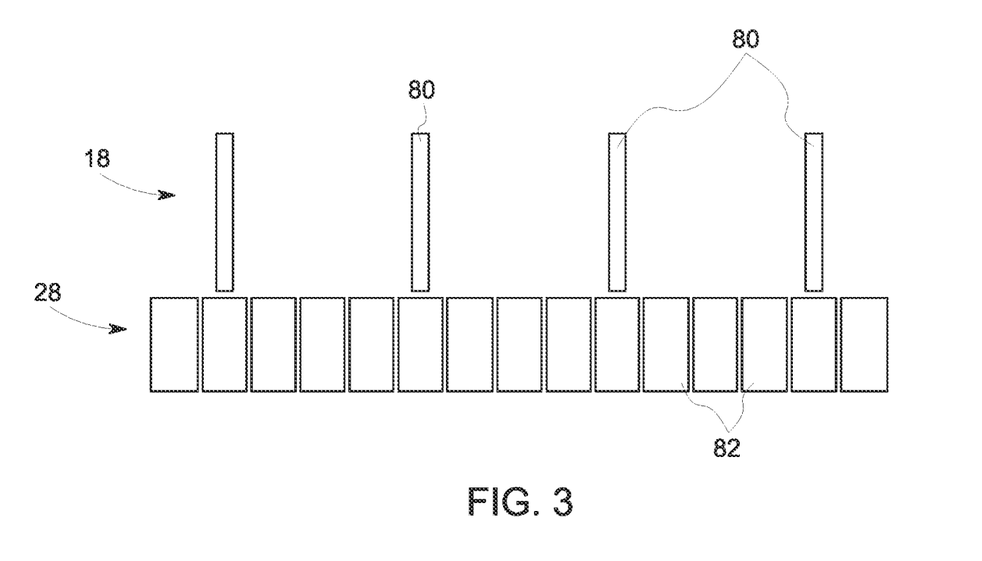
FIG. 3 depicts schematically an additional side-view of channels of a detector on which collimator blades are disposed, in accordance with aspects of the present disclosure.

Turning to FIG. 3, an example of a higher spatial resolution detector 28 having smaller pixels 82 (e.g., a pixel pitch less than 1 mm). Due to the smaller pixels, each channel may not be separated by respective collimator blades. Instead as shown, each collimator blade 80 may provide collimation for multiple pixels 82 (i.e., channels), with some pixels 82 touched by or immediately adjacent a blade 80 and others not adjacent a blade 80. Correspondingly, in the event of an X-ray focal spot mis-alignment the differential gain change due to X-ray focal spot mis-alignment between adjacent channels may be large due to the different placement of the relevant blade 80. That is, X-ray focal spot mis-alignment may result in large gain changes in high resolution detectors.

Figure 4:
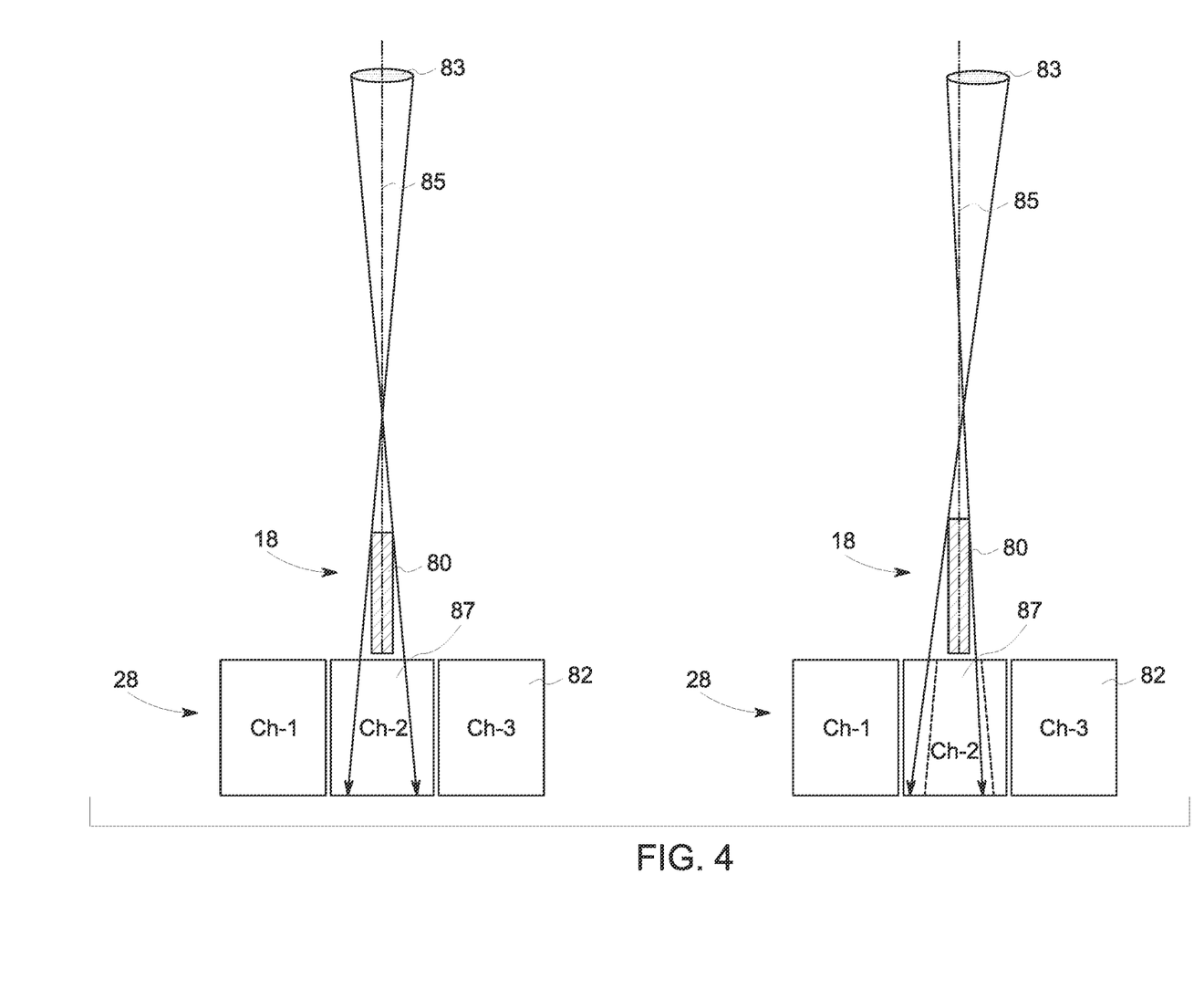
FIG. 4 depicts schematically an aligned and mis-aligned X-ray focal spot in the context of a collimated radiation detector, in accordance with certain aspects of the present disclosure.

Conceptually, this is illustrated on FIG. 4, where a side-by-side comparison of an aligned (left) and mis-aligned (right) X-ray focal spot 83 are illustrated in the context of a collimated detector 28. As shown in the left figure, when the X-ray focal spot 83 is aligned (as denoted by longitudinal axis 85 extending through the blade 80) with the blade 80, the shadow 87 cast by the blade 80 is generally symmetric and minimized. Conversely, as shown on the right, when the X-ray focal spot 83 is misaligned with respect to the blade 80, the shadow 87 cast by the blade 80 is not symmetric with respect to different pixels 82 (denoted here as channels (CH)-1, -2, -3) and may be increased in size relative to when the X-ray focal spot 83 is aligned.

With the preceding discussion in mind, the mis-alignment of the collimator blade 80 and the X-ray focal spot 83 may result in image artifacts that are detrimental to clinical image quality. In particular, the effect of mis-alignment at the detector level is the introduction of small, but impactful changes in the gain of individual channels due to collimator blade shadowing of the X-ray focal spot, as shown in FIG. 4. That is, incremental change to the collimator blade shadow on the respective detector channels may lead to differential changes in channel gain, which can result in image artifacts. As illustrated with respect to FIGS. 2-4, this effect may be more significant in contexts where the pitch of the collimator blades 80 is greater that the pixel (i.e., channel) pitch such that there are pixels with a collimator blade above them and pixels without such a blade above them. If not detected and corrected, these changes due to X-ray focal spot mis-alignment may be wrongly interpreted as changes in object attenuation, thereby leading to image artifacts.

In practice, X-ray focal spot misalignment may be of two types. Static mis-alignment, as used herein, may be understood to be due to manufacturing tolerances, such as with respect to the deflection or tilt of collimator blades, and can be corrected to some extent by detector calibration. However, dynamic mis-alignment, may occur during the course of a scan due to thermal and mechanical forces generated during operation. Dynamic misalignment can be difficult to detect and, correspondingly, challenging to correct.

With the preceding in mind, the techniques discussed herein may be used to detect and correct channel gain errors attributable to X-ray focal spot misalignment during the course of a scan, including in higher resolution type system, as shown in FIG. 3. In particular, the techniques disclosed herein may be performed without additional hardware for the detection of X-ray focal spot drift.

Figure 5:
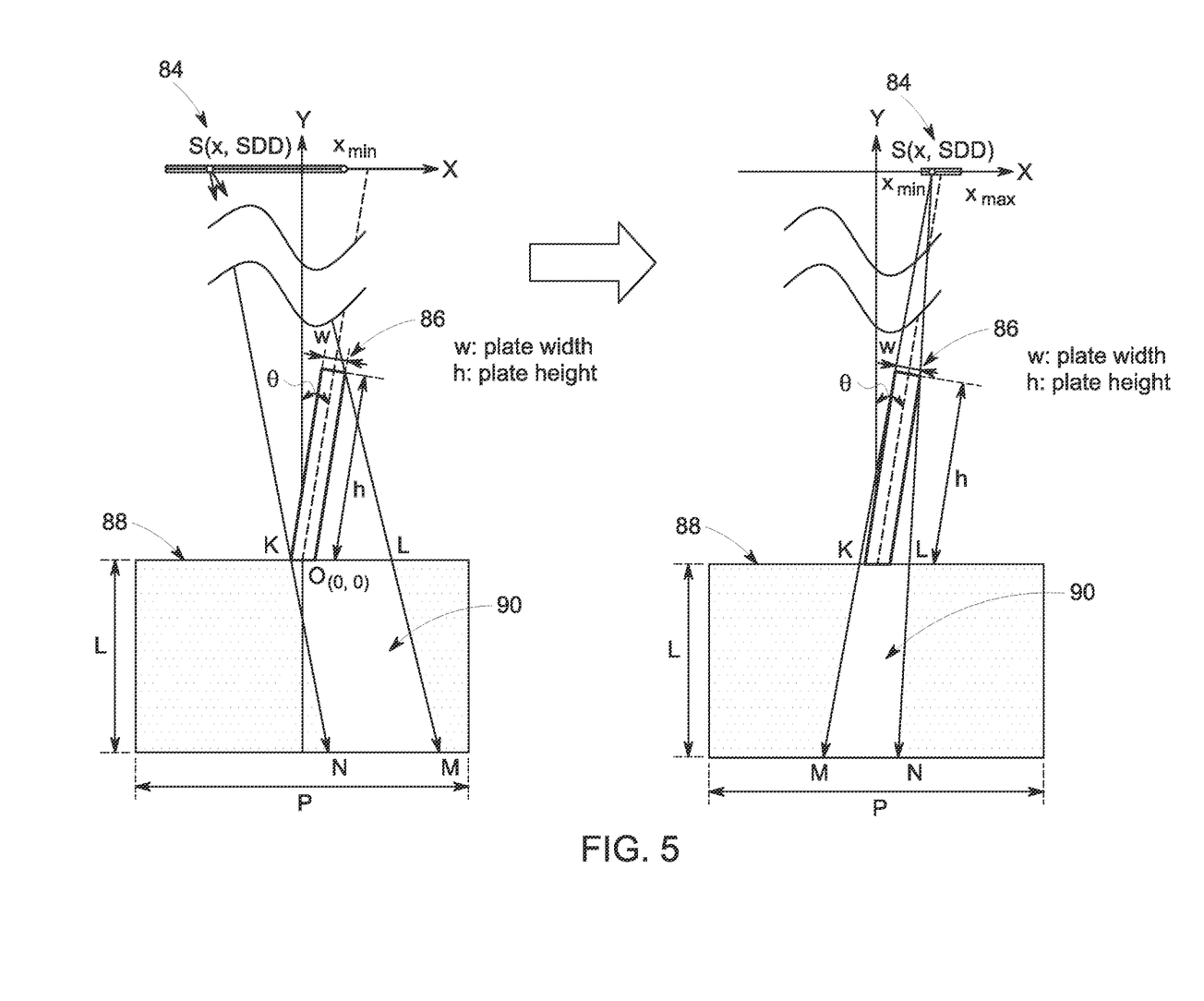
FIG. 5 depicts schematically the effect of X-ray focal spot motion on pixel gain, in accordance with certain aspects of the present disclosure.
Figure 6:
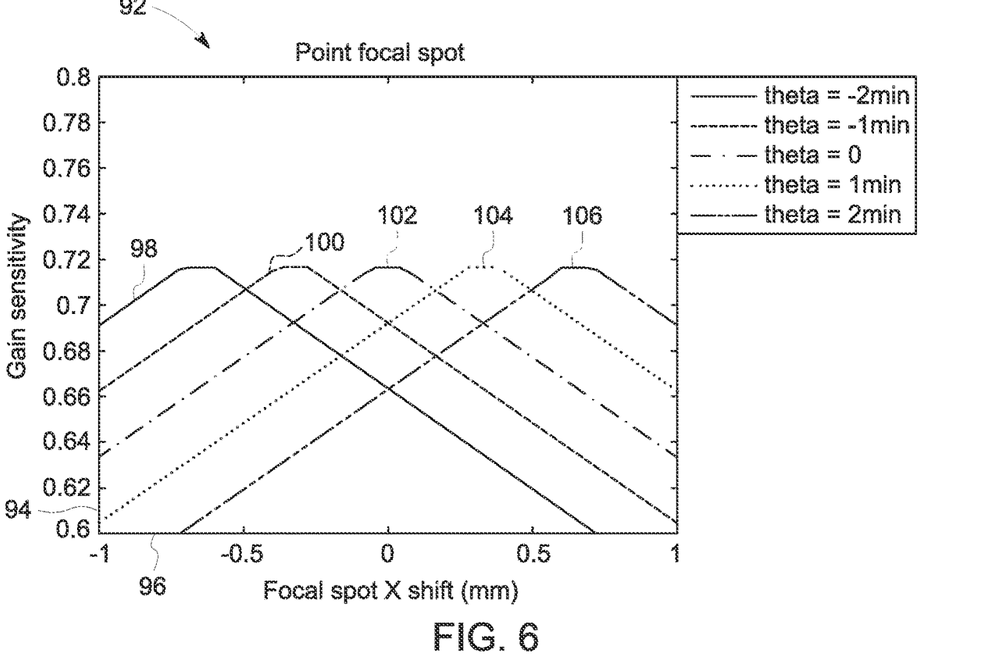
FIG. 6 depicts graphically the gain sensitivity function due to X-motion of the X-ray focal spot, in accordance with certain aspects of the present disclosure.

As illustrated in FIGS. 5 and 6, pixels on which a collimator blade is present are affected by X-ray focal spot misalignment (e.g., motion). FIG. 5 depicts the X-ray focal spot 84 (represented as S (x, source to detector distance (SDD)) and the tilted collimator blade 86 disposed over a pixel or channel 88. When the X-ray focal spot 84 shifts from the left of the tilted collimator blade 86 (as depicted in left figure) to the right of the tilted collimator blade 86 (as depicted in the right figure), a shadow 90 (e.g., signal lost by pixel 88) cast by the blade 86 changes in size and shape (which means the pixel or channel gain also changes). For a point focal spot the pixel gain, g, experienced by the pixel 88 with the tilted collimator blad 86 is represented by the following X-motion gain sensitivity function g(x, θ), where w represent plate width, h represents plate height, p represents pixel or channel pitch, and θ represents the tilt of the collimator blade 86:

$$g(x,\theta) \sim 1 + \frac{h}{p \cdot SDD}x - \left(1 + \frac{h}{2SDD}\right)\frac{w}{p} - \left(1 + \frac{h}{SDD}\right)\frac{h}{p}\theta, \quad (1)$$

$$x < x_{min} = SDD \cdot \tan\theta - \frac{w}{2}\cos\theta;$$

$$g(x,\theta) \sim 1 - \left(1 + \frac{h}{SDD}\right)\frac{w}{p}, \quad x_{min} < x < x_{max}; \text{ and} \quad (2)$$

$$g(x,\theta) \sim 1 - \frac{h}{p \cdot SDD}x - \left(1 + \frac{h}{2SDD}\right)\frac{w}{p} + \left(1 + \frac{h}{SDD}\right)\frac{h}{p}\theta, \quad (3)$$

$$x > x_{max} = SDD \cdot \tan\theta + \frac{w}{2}\cos\theta.$$

FIG. 6 depicts a graph 92 of the X-motion gain sensitivity function for a particular pixel having a collimator blade disposed over it at different tilt angles (θ). The graph 92 includes a Y-axis 94 representing gain sensitivity and an X-axis 94 representing X-ray focal spot shift in the X-direction. For the plots 98, 100, 102, 104, and 106, the collimator blade is at different tilt angles (θ) (represented as fraction of a minute). As depicted, pixel gain is a linear function of X-ray focal spot location for large shifts in the X-direction (represented by the sloped or inclined portions of the plots 98, 100, 102, 104, and 106), while the pixel gain is constant for smaller shifts in the X-direction represented by the plateaus of the plots 98, 100, 102, 104, and 106. The shapes are the same for the plots 98, 100, 102, 104, and 106 but the plots 98, 100, 102, 104, 106 shift based on the plate tilt angle. The slope of the plots 98, 100, 102, 104, and 106 are independent of the plate tilt angle.

Figure 7:
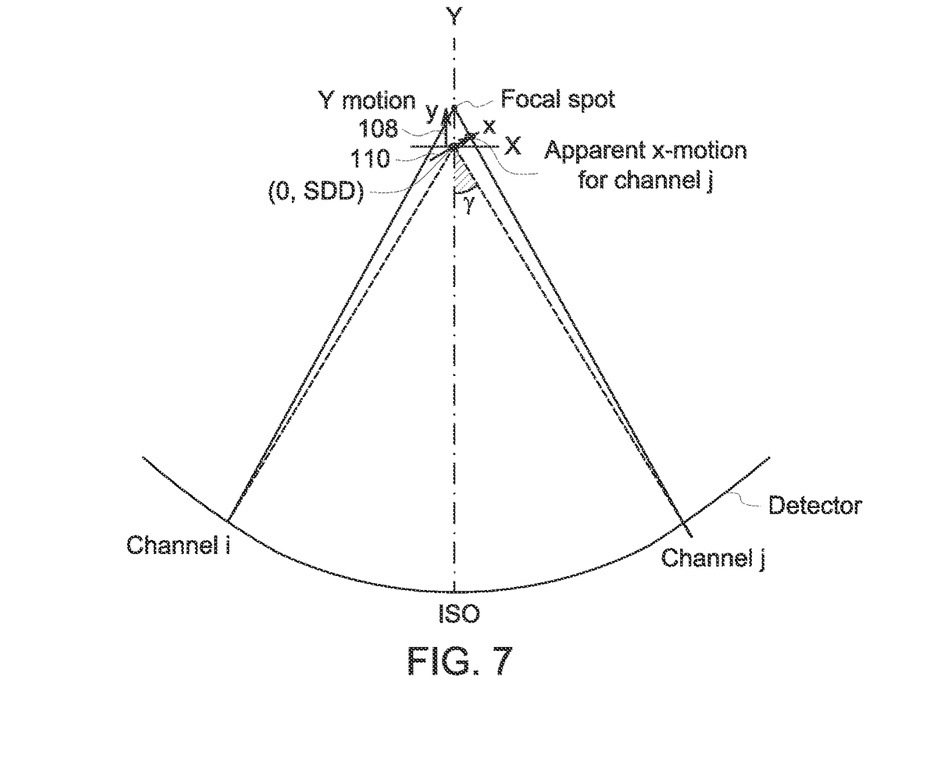
FIG. 7 depicts schematically apparent X-motion of the X-ray focal spot induced by Y-motion of the X-ray focal spot, in accordance with certain aspects of the present disclosure.

As depicted in FIG. 7, for certain pixels or channels, motion of the X-ray focal spot in the Y-direction (indicated by arrow 108 and along a direction of the X-rays) relative to an isocenter (ISO) of the detector may experience apparent motion in the X-direction (indicated by arrow 110 and along an arc of the detector) relative to an isocenter. Channels further away from the isocenter (e.g., channels i and j in FIG. 7), such as those channels closer to an edge of the detector, may experience the apparent motion in the X-direction. Channels closer to the isocenter may be experience negligible apparent motion in the X-direction. In FIG. 7, channels i and j are equidistant from the isocenter at fan angles −γ and +γ. A channel at the isocenter may be designated channel ISO. Channels i, j, and ISO include tilted collimator blades disposed over them. The induction of apparent motion in the X-direction due to motion in the Y-direction is proportional to the sine of the fan angle, γ, and may be represented by the following equation:

$$x(\text{motion}) \sim y \cdot \sin(\Gamma), \quad (4)$$

where x represents the apparent motion in the X-direction and y represents the motion in the Y-direction for the X-ray focal spot.

Figure 8:
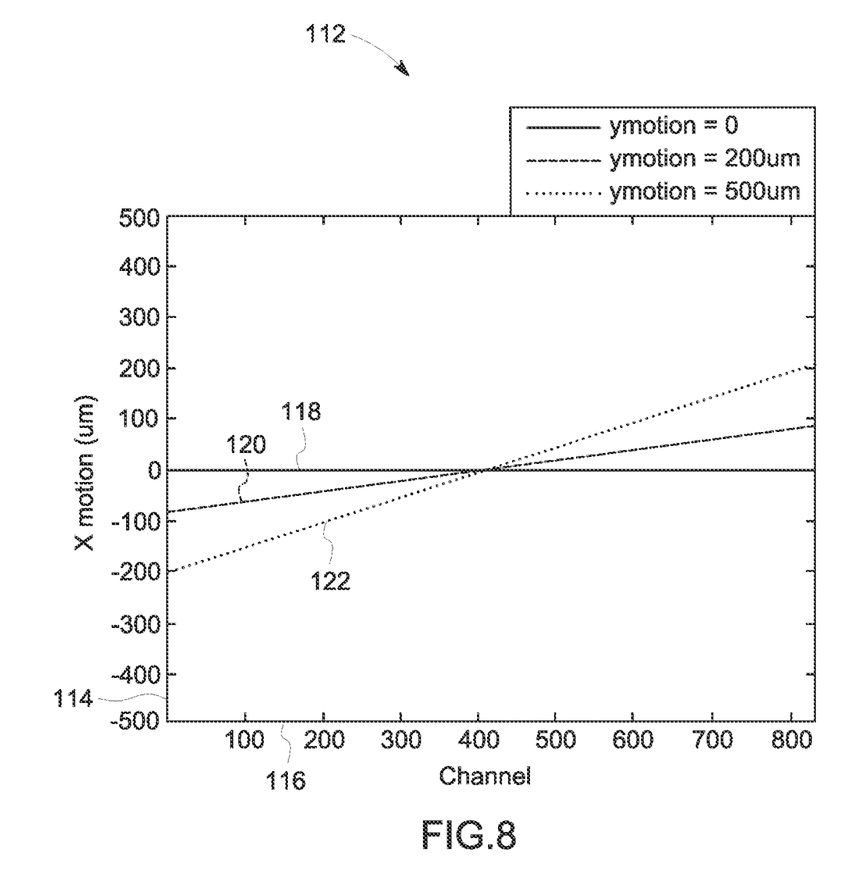
FIG. 8 depicts graphically apparent X-motion of the X-ray focal spot induced by Y-motion of the X-ray focal spot, in accordance with certain aspects of the present disclosure.

FIG. 8 depicts a graph 112 of apparent motion in the X-direction of an X-ray focal spot experienced by channels of a detector in response to motion in the Y-direction of the X-ray focal spot utilizing equation (4). The graph 112 includes a Y-axis 114 representing apparent motion of the X-ray focal spot in the X-direction and an X-axis 116 representing the channels of a detector (e.g., with an isocenter being near channel 400). Plots 118, 120, and 122 represent different amounts of motion of the X-ray focal spot in the Y-direction. As depicted in graph 112, the y-motion induced apparent X motion of the X-ray focal spot (as determined via equation (4)) is an asymmetric function. As depicted in graph 112, in the presence of Y-motion of the X-ray focal spot, the apparent X-motion increases as the distance from the isocenter increases (both to the left and right of the isocenter). In the presence of Y-motion of the X-ray focal spot, the apparent X-motion is the same at equal distances to the left and right of the isocenter but different in direction. Also, as depicted in graph 112, as the magnitude of Y-motion of the X-ray focal increases, the apparent X-motion increases for a given channel.

Returning to FIG. 7, X-ray focal spot motion in both the X-direction and the Y-direction relative to the isocenter will result in a net or total focal spot motion (x) in the X-direction for the channels i and j, respectively, represented by the following:

$$x = x_X + x_Y = x_X \pm y \cdot \sin(\gamma) \quad (5)$$

The asymmetric dependence of Y motion induced channel gain, g, on the distance of the channel from the isocenter can be utilized to extract both X motion and Y motion of the X-ray focal spot by the following:

$$\frac{g_j - g_i}{2} \xrightarrow{yields} x_Y(Y \text{ motion}) \text{ and} \quad (6)$$

$$\frac{g_j + g_i}{2} \xrightarrow{yields} x_X(X \text{ motion}). \quad (7)$$

Figure 9:
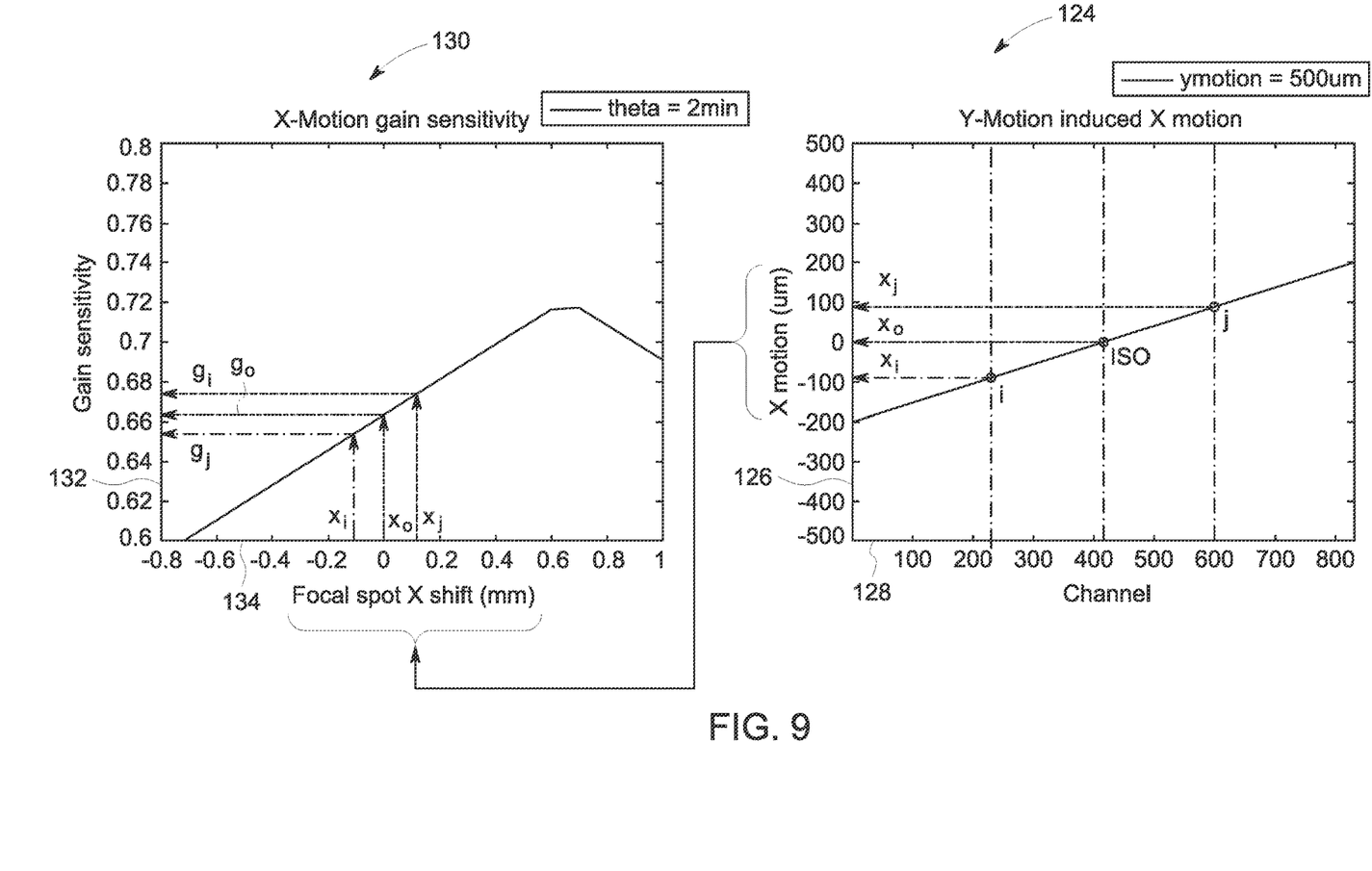
FIG. 9 depicts graphically the effect of Y-motion induced X-motion on the X-motion gain sensitivity on channels with tilted collimator plates, in accordance with certain aspects of the present disclosure.

This asymmetric dependence of Y motion induced channel gain, g, on the distance of the channel from the isocenter to extract or detect both X motion and Y motion of the X-ray focal spot is illustrated in FIG. 9. Graph 124 depicts the Y-motion induced X motion (apparent X-motion) for channels i and j and channel at the isocenter, channel ISO, of the detector in FIG. 7. Graph 124 includes a Y-axis 126 representing X motion and an X-axis 128 representing the channels of a detector (e.g., with an isocenter being near channel 400). The graph 124 illustrates the Y motion induced X motion $x_j$, $x_o$, and $x_j$ for channels i, ISO, and j, respectively. Graph 130 depicts the gain sensitivity (and linear gain response) for channels i, j, and ISO in response to the Y-motion induced X-motion shown in graph 124. Graph 130 includes a Y-axis 132 representing gain sensitivity and an X-axis 134 representing the focal spot shift in the X-direction. The gain sensitivities for the channels i, j, and ISO are $g_j$, $g_o$, and $g_i$, respectively. The linear gain response of the channels with titled collimator plates (e.g., channels i, ISO, and j) may be utilized in detecting X-motion and Y-motion of the X-ray focal spot.

Figure 10:
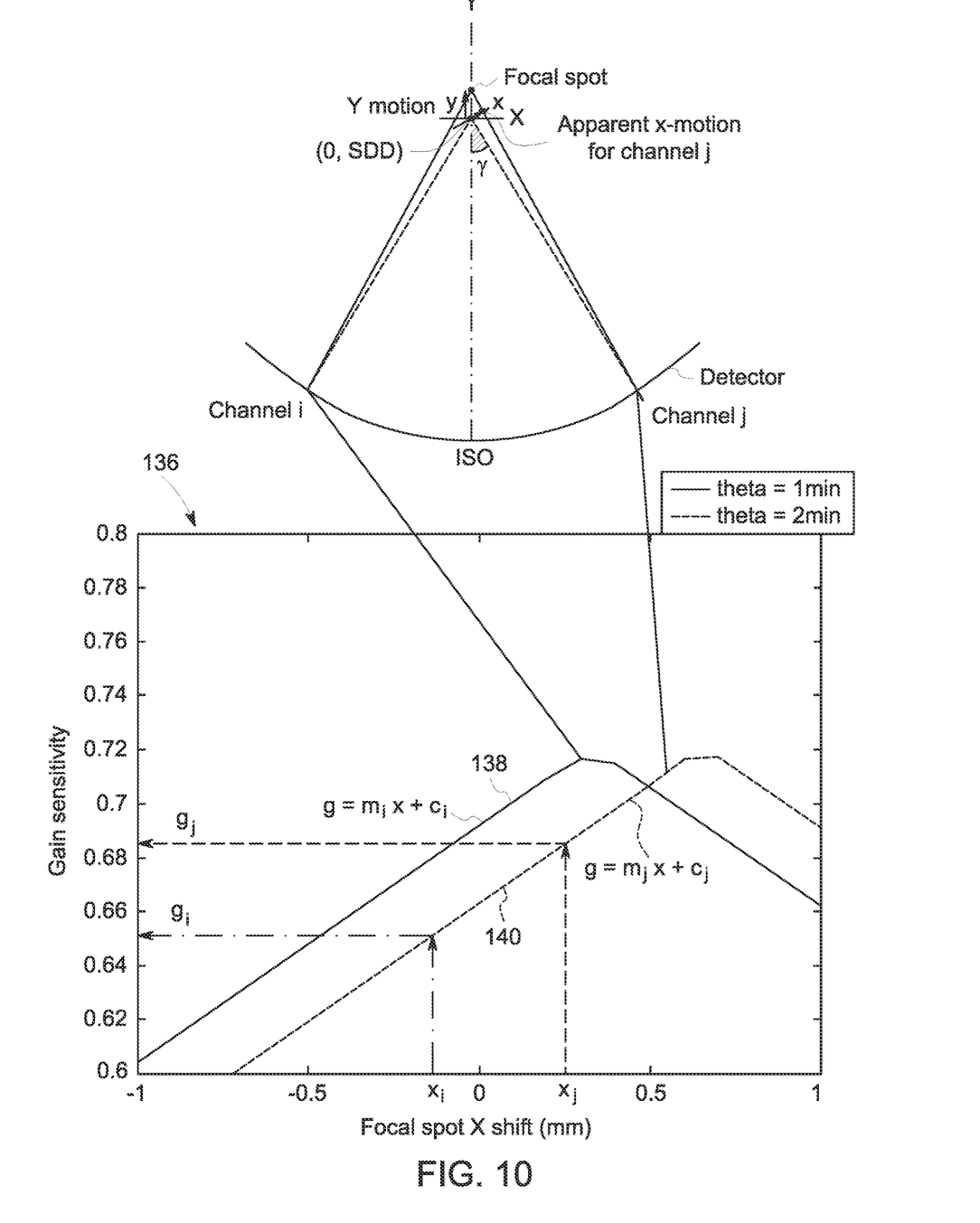
FIG. 10 depicts schematically and graphically the linear tilted gain responses for channels of a detector in response to total X-ray focal spot shift in the X-direction, in accordance with certain aspects of the present disclosure.

Based on these relationships discussed above, an algorithm may be utilized to detect X-motion and Y-motion of the X-ray focal spot. In particular, X-motion and Y-motion may be estimated independently from two simultaneous measurements. FIG. 10 illustrates some of the definitions utilized in the following discussion by relating the schematic of FIG. 7 to a graph 136 that illustrates the linear tilted gain responses for channels i and j in response to total X-ray focal spot shift in the X-direction. The respective total X-motion for channels i and j are $$x_i = x_{Xi} + x_{Yi} \text{ and} \quad (8)$$

$$x_j = x_{Xj} + x_{Yj}, \quad (9)$$

where $x_x$ and $x_y$ represent intrinsic X-motion and apparent X-motion, respectively. The respective tilted blade gain responses (e.g., linear gain responses) for channels i and j (shown as plots 138 and 140, respectively, in graph 136) are $$g_i = m_i x_i + c_i \text{ and} \quad (10)$$

$$g_j = m_j x_j + c_j, \quad (11)$$

where m represents the slope and c the vertical intercept. These equations can be further simplified due to symmetry. For example, intrinsic x-motion is same for $\forall i$, thus:

$$x_{Xi} = x_{Xj} = x_x \text{ and} \quad (12)$$

$$x_{Yj} = y \cdot \sin(\gamma) = -x_{Yi} = x_y. \quad (13)$$

Also, Y-motion of the X-ray focal spot is anti-symmetric, thus:

$$x_i = x_X - x_Y \text{ and} \quad (14)$$

$$x_j = x_X + x_Y. \quad (15)$$

Further, the slopes $m_j$ and $m_i$ are identical, thus, $$m_i = m_j = m = \frac{h}{(p \cdot SDD)}. \quad (16)$$

Based on these equations, both the X-motion and the Y-motion of the X-ray focal spot may be estimated independently. The X-motion may be estimated utilizing the following:

$$\bar{x} = x_X = \frac{\bar{x}_j + \bar{x}_i}{2} = \frac{(g_j + g_i) - (c_j + c_i)}{2m}. \quad (17)$$

The Y-motion may be estimated utilizing the following:

$$\bar{y} = \frac{x_Y}{\sin(\gamma)} = \frac{(g_j - g_i) - (c_j - c_i)}{2m \cdot \sin(\gamma)}, \text{ where} \quad (18)$$

$$x_Y = \frac{\bar{x}_j - \bar{x}_i}{2}. \quad (19)$$

In certain embodiments, the channels with tilted blade gain responses utilized in determining X-ray focal spot motion may have the same tilt angles but opposite orientations since the channels are located on opposite sides of the isocenter of the detector. In other embodiments, as indicated in graph 136, the channels (e.g., channels i and j) with the tilted blade gain responses utilized in determining X-ray focal spot motion may have different tilt angles as well as opposite orientations. Although it is preferable to utilize channels with collimator plates that are equidistance from the isocenter of the detector (e.g., at fan angles −γ and +γ), in certain embodiments, the channels with tilted blade gain response utilized in determining X-ray focal spot may not be equidistant from the isocenter of the detector.

Figure 11:
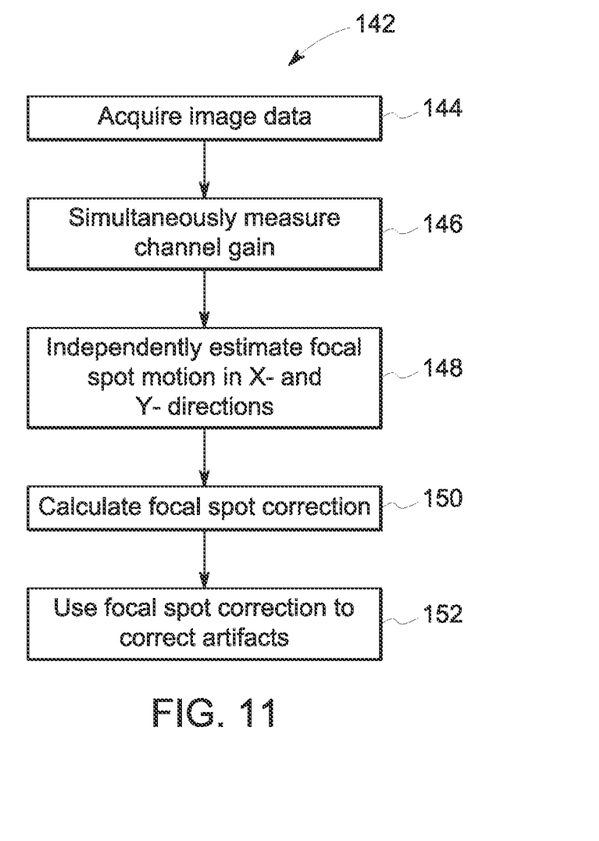
FIG. 11 depicts a flow chart of a method for detecting and correcting for X-ray focal spot motion, in accordance with certain aspects of the present disclosure.

FIG. 11 depicts a flow chart of a method 142 for detecting and correcting for X-ray focal spot motion. One or more steps of the method 142 may be performed by the CT imaging system 10 of FIG. 1. The method 142 includes acquiring image data (e.g. CT scan data) by causing X-ray to be emitted from an X-ray focal spot of an X-ray source toward a radiation detector including multiple channels or pixels (block 144). A first subset of the channels each have a collimator blade positioned above a respective channel, while a second subset of channels are unobstructed by collimator blades. The method 142 also includes simultaneously measuring respective channel gain for a first channel and a second channel of the subset of channels having a collimator blade disposed over them (block 146). The measuring of the channel gain may occur as image data is being acquired. The first channel and second channel are disposed on opposite sides of an isocenter of the detector. In certain embodiments, the first and second channels are disposed equidistant from the isocenter of the detector. In other embodiments, the first and second channels are not equidistant from the isocenter of the detector. In certain embodiments, in order to measure the respective channel gain, the method 142 includes determining a respective total X-ray focal spot motion in the X-direction for both the first channel and the second channel from which the channel gain can be determined. The total X-ray focal spot motion includes a summation of intrinsic X-ray focal spot motion in the X-direction and apparent X-ray focal spot motion (inducted by Y-motion of the X-ray focal spot) in the X-direction. The method 142 further includes independently estimating X-ray focal spot motion in both the X-direction and the Y-direction relative to the isocenter based on the respective channel gains for the first channel and the second channel (block 148). The method 142 even further includes calculating a focal spot motion correction factor(s) based on the estimates X-ray focal spot motion in the X-direction and the Y-direction (block 150). The method 142 still further includes using the focal spot motion correction factor(s) as part of the image reconstruction or post-reconstruction process, to correct or remove artifacts or other image irregularities (block 152). By way of example, in certain embodiments signal correction may be limited to those channels associated with a pixel on a collimator plate is positioned, i.e., those channels where signal change may be due to misalignment of the collimator blades. Alternatively, in certain embodiments, based on the estimates of X-ray focal spot motion in the X-direction and the Y-direction, the X-ray focal spot location may be actively controlled or corrected (e.g., via magnets that steer the electron beam toward an anode).

Technical effects of the disclosed embodiments include providing a CT imaging system capable of reducing the effects of X-ray focal spot motion during an imaging operation, such as by reducing or eliminating image artifacts attributable to X-ray focal spot motion. Estimation and/or correction of X-ray focal spot motion effects are achieved without additional hardware.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for estimating motion of an X-ray focal spot, comprising the acts of:
acquiring image data by causing X-rays to be emitted from the X-ray focal spot of an X-ray source toward a radiation detector comprising a plurality of channels, wherein a subset of the channels each have a collimator blade positioned above the respective channel; and
independently estimating X-ray focal spot motion both in an X-direction for the X-ray focal spot relative to an isocenter of the radiation detector based on respective channel gains for a first channel and a second channel of the subset of the channels and in a Y-direction along a direction of the X-rays for the X-ray focal spot relative to the isocenter based on the respective channel gains for the first channel and the second channel of the subset of the channels.

2. The method of claim 1, wherein the first channel and the second channel are equidistant from the isocenter.

3. The method of claim 1, further comprising estimating a respective total X-ray focal spot motion in the X-direction for the first channel and the second channel.

4. The method of claim 3, wherein the respective total X-ray focal spot motion comprises a summation of an intrinsic X-ray focal spot motion in the X-direction and apparent X-ray focal spot motion in the X-direction.

5. The method of claim 4, wherein the intrinsic X-ray focal spot motion in the X-direction is the same for the first channel and the second channel.

6. The method of claim 5, wherein the respective apparent X-ray focal spot motions in the X-direction for the first channel and the second channel are anti-symmetric.

7. The method of claim 6, wherein the respective apparent X-ray focal spot motions for the first channel and the second channel are each a product of respective X-ray focal motion in the Y-direction and a respective sine of a fan angle for the first channel and the second channel.

8. The method of claim 1, further comprising:
calculating a focal spot motion correction based on the estimates of X-ray focal spot motion in the X-direction and the Y-direction; and
using the focal spot motion correction as part of an image reconstruction or post-reconstruction process to correct or remove artifacts or other image irregularities.

9. An imaging system, comprising:
an X-ray source configured to emit X-rays from an X-ray focal spot during operation;
a collimator comprising a plurality of collimator blades;
a radiation detector, comprising a plurality of pixels, each pixel corresponding to a channel of the radiation detector, wherein a subset of the channels each have a collimator blade positioned above the respective channel; and
processing circuitry configured to perform acts comprising:
acquiring image data by causing X-rays to be emitted from the X-ray source toward the radiation detector; and
independently estimating X-ray focal spot motion both in an X-direction for the X-ray focal spot relative to an isocenter of the radiation detector based on respective channel gains for a first channel and a second channel of the subset of the channels and in a Y-direction for the X-ray focal spot relative to the isocenter based on the respective channel gains for the first channel and the second channel of the subset of the channels.

10. The imaging system of claim 9, wherein the first channel and the second channel are equidistant from the isocenter.

11. The imaging system of claim 9, wherein the processing circuitry is configured to perform further acts further comprising estimating a respective total X-ray focal spot motion in the X-direction for the first channel and the second channel.

12. The imaging system of claim 11, wherein the respective total X-ray focal spot motion comprises a summation of an intrinsic X-ray focal spot motion in the X-direction and apparent X-ray focal spot motion in the X-direction.

13. The imaging system of claim 12, wherein the intrinsic X-ray focal spot motion in the X-direction is the same for the first channel and the second channel.

14. The imaging system of claim 13, wherein the respective apparent X-ray focal spot motions in the X-direction for the first channel and the second channel are anti-symmetric.

15. The imaging system of claim 14, wherein the respective apparent X-ray focal spot motions for the first channel and the second channel are each a product of respective X-ray focal motion in the Y-direction and a respective sine of a fan angle for the first channel and the second channel.

16. The imaging system of claim 9, wherein the processing circuitry is configured to perform further acts further comprising:
calculating a focal spot motion correction based on the estimates of X-ray focal spot motion in the X-direction and the Y-direction; and
using the focal spot motion correction as part of an image reconstruction or post-reconstruction process to correct or remove artifacts or other image irregularities.

17. A non-transitory computer-readable medium, the computer-readable medium comprising processor-executable code that when executed by a processor, causes the processor to:
acquire image data by causing X-rays to be emitted from an X-ray focal spot of an X-ray source toward a radiation detector comprising a plurality of channels, wherein a subset of the channels each have a collimator blade positioned above the respective channel;
simultaneously measure a respective channel gain for a first channel and a second channel of the subset of channels disposed on opposite sides of an isocenter of the radiation detector; and
independently estimate X-ray focal spot motion both in an X-direction for the X-ray focal spot relative to the isocenter based on the respective channel gains for the first channel and the second channel and in a Y-direction for the X-ray focal spot relative to the isocenter based on the respective channel gains for the first channel and the second channel.

18. The non-transitory computer-readable medium of claim 17, wherein the first channel and the second channel are equidistant from the isocenter.

19. The non-transitory computer-readable medium of claim 17, wherein the processor-executable code when executed by the processor, causes the processor to estimate a respective total X-ray focal spot motion in the X-direction for the first channel and the second channel, wherein the respective total X-ray focal spot motion comprises a summation of an intrinsic X-ray focal spot motion in the X-direction and apparent X-ray focal spot motion in the X-direction.

20. The non-transitory computer-readable medium of claim 17, wherein the processor-executable code when executed by the processor, causes the processor to:
calculate a focal spot motion correction based on the estimates of X-ray focal spot motion in the X-direction and the Y-direction; and
use the focal spot motion correction as part of an image reconstruction or post-reconstruction process to correct or remove artifacts or other image irregularities.

* * * * *